US009603366B2

(12) United States Patent
Lovatt

(10) Patent No.: US 9,603,366 B2
(45) Date of Patent: *Mar. 28, 2017

(54) USE OF 9-BETA-D-ADENOSINE TO INCREASE CROP PRODUCTION

(71) Applicant: The Regents of the University of California, Oakland, CA (US)

(72) Inventor: Carol J. Lovatt, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/880,120

(22) Filed: Oct. 9, 2015

(65) Prior Publication Data

US 2016/0088842 A1    Mar. 31, 2016

Related U.S. Application Data

(63) Continuation of application No. 14/503,276, filed on Sep. 30, 2014, now abandoned, which is a continuation of application No. 13/519,889, filed as application No. PCT/US2010/062267 on Dec. 28, 2010, now Pat. No. 8,846,572.

(60) Provisional application No. 61/290,473, filed on Dec. 28, 2009.

(51) Int. Cl.
*A01N 43/90*    (2006.01)
*C05F 11/10*    (2006.01)
*A01N 57/16*    (2006.01)
*C05B 17/00*    (2006.01)
*C05G 3/00*    (2006.01)

(52) U.S. Cl.
CPC ............ *A01N 43/90* (2013.01); *A01N 57/16* (2013.01); *C05B 17/00* (2013.01); *C05F 11/10* (2013.01); *C05G 3/00* (2013.01)

(58) Field of Classification Search
None
See application file for complete search history.

(56) References Cited

U.S. PATENT DOCUMENTS

| | | |
|---|---|---|
| 3,830,643 A | 8/1974 | Schneider et al. |
| 4,209,316 A | 6/1980 | McDaniel et al. |
| 4,741,754 A | 5/1988 | Ries |
| 5,009,698 A * | 4/1991 | Ries ............... A01N 43/90 504/241 |
| 5,217,738 A | 6/1993 | Ries |
| 5,234,898 A | 8/1993 | Ries |
| 6,169,057 B1 | 1/2001 | Lovatt |
| 6,180,569 B1 | 1/2001 | Lovatt |
| 6,874,277 B2 | 4/2005 | Yamashita |
| 7,160,350 B2 | 1/2007 | Lovatt |
| 8,846,572 B2 | 9/2014 | Lovatt |
| 9,044,018 B2 | 6/2015 | Lovatt |
| 2002/0121046 A1 | 9/2002 | Yamashita |
| 2004/0192553 A1 * | 9/2004 | Kurauchi ............... A01N 43/90 504/292 |
| 2004/0209777 A1 | 10/2004 | Gemma et al. |

FOREIGN PATENT DOCUMENTS

| | | |
|---|---|---|
| EP | 0190885 A2 | 8/1986 |
| EP | 0199474 A2 | 10/1986 |
| EP | 0508777 A2 | 10/1992 |
| JP | 48-26517 Y1 | 8/1973 |
| JP | 48067051 A * | 9/1973 |
| JP | 54-17670 B1 | 7/1979 |
| JP | 62-249978 A | 10/1987 |
| WO | 79/00838 A1 | 10/1979 |
| WO | 2011/090726 A2 | 7/2011 |
| WO | 2011/090727 A2 | 7/2011 |
| WO | 2011/090726 A3 | 11/2011 |
| WO | 2011/090727 A3 | 11/2011 |

OTHER PUBLICATIONS

Kobayashi et al., "Fruit-Setting and Fruit Enlargement Promoting Agent (Full Translation)," Translated by Poenix Translations, Jan. 2014, p. 1-8.*
IFDC, "What are fertilizers?" <http://ifdc.org/Media_Center/Fertilizer_FAQs>, published Jun. 24, 2012, p. 1-3.*
Sigma-Aldrich, "Adenosine Material Safety Data Sheet (Product No. A9251)," Version 5.0, Revision Date Jun. 16, 2012, p. 1-6.*
Cox, T.P., "Perennial upland rice takes root", <http://www.new-ag.info/en/developments/devItem.php?a=798>, published Jul. 2009, p. 1-2.*
Dixon et al., "The Impact of Foliar Applications of Nitrogen and Boron on 'Hass' Avocado Fruit Set in 2004", New Zealand Avocado Grower's Association Annual Research Report, vol. 5, 2005, pp. 27-33.
Gonzalez et al., "Properly Timed Foliar Fertilization Can and Should Result in a Yield Benefit and Net Increase in Grower Income", ISHS Acta Horticulturae, vol. 868, 2010, pp. 273-286.
Guardiola, "Increasing Citrus Fruit Size With Synthetic Auxins", Departamento de Biologia Vegetal, Universidad Politecnica de Valencia. Valencia. Spain, 1997, pp. 79-86.
Han et al., "A Novel Inhibitor of 9-cis-Epoxycarotenoid Dioxygenase in Abscisic Acid Biosynthesis in Higher Plants", Plant Physiology, vol. 135, Jul. 2004, pp. 1574-1582.
Ito et al., "Studies on the Physiological Responses of Crop Plants following Application of Exogenous Nucleic Acid Components. I. Effect of Exogeneous Nucleic Acid Components on the Germination of Seeds and the Growth of Seeding during the Early Stages of the Rice Plan, Oryza Stativa". Database Accession No. 85:42078, May 12, 1984, 2 pages.

(Continued)

*Primary Examiner* — Tracy Vivlemore
*Assistant Examiner* — Monica Shin
(74) *Attorney, Agent, or Firm* — Morrison & Foerster LLP

(57) ABSTRACT

Described are compositions and methods to increase bud break in order to increase aspects of one or both of plant vegetative and reproductive growth, by use of a natural metabolite. In particular, the present disclosure provides a natural metabolite either alone or as part of a fertilizer blend to increase crop production. Additionally the present disclosure provides a natural metabolite in combination with one or both of a plant growth regulator and a bio stimulant to increase crop production.

17 Claims, 2 Drawing Sheets

(56) References Cited

OTHER PUBLICATIONS

Jaganath et al., "Efficacy Studies on Prebloom Canopy Applications of Boron and/or Urea to 'Hass' Avocados in California", Proceedings of the World Avocado Congress III, 1995, pp. 181-184.
Khoshbakht et al., "How Many Plant Species are Cultivated?", Genet Resour. Crop. Evol., vol. 55, 2008, pp. 925-928.
Kobayashi et al., "Growth Promoting Agents for Vegetables and Grains", Database Accession No. 80:44694, May 12, 1984, 2 pages.
Lovatt et al., "Improving the Efficacy of GA3 to Increase Fruit Set and Yield of Clementine Mandarins in California", 2007 Annual Report, Plant Management & Physiology, Citrus Research Board, 2007, pp. 9-17.
Lovatt, "Plant Growth Regulators for Avocado Productin", California Avocado Society 2005 Yearbook, vol. 88: 81-91, 2005, 7 pages.
Lovatt, "Timing Citrus and Avocado Foliar Nutrient Applications to Increase Fruit Set and Size", Hort Technology, vol. 9, No. 4, Oct.-Dec. 1999, pp. 607-612.
Lovatt et al., "Developing Field Strategies to Correct Alternate Bearing", 2008 Production Research Report, Management and Physiology, California Avocado Commission, 2008, 6 pages.
Lovatt et al., "PGR Strategies to Increase Fruit Size of 'Hass' Avocado", 2008 Production Research Report, Management and Physiology, California Avocado Commission, 2008, 3 pages.
Lovatt et al., "PGR Strategies to Increase Yield of 'Hass' Avocado", 2008 Production Research Report,Management and Physiology, California Avocado Commission, 2008, 7 pages.
Lovatt et al., "UC IPM: Plant Growth Regulators in Citrus: General Information", available at <http://www.ipm.ucdavis.edu/PMG/r107900111.html>, accessed on Apr. 11, 2013, 3 pages.
Lovatt et al., "Urea Combined with 6-Benzyladenine to Reduce Alternate Bearing in Pistachio and to Increase Cumulative Yield", Extension Pomologist, Univ. of California, Davis/Kearny Agricultural Center, 2001, pp. 346-356.
My Agriculture Information Bank, "Classification of Crop Plants", retrieved from Internet on Aug. 7, 2013 <http:/ I agriinfo .in/?page=topic&superid= 1 &topicid=309>, Aug. 7, 2013, 3 pages.
Ries et al., "9-β-L(+) Adenosine: A New Naturally Occurring Plant Growth Substance Elicited by Triacontanol in Rice", Plant Growth Regulation, vol. 9, No. 3, Aug. 1990, pp. 263-273.
Ries, "Triacontanol and Its Second Messenger 9-β-L(+)-Adenosine as Plant Growth Substances", Plant Physiol., vol. 95, 1991, pp. 986-989.
"The Growth Stages of the Rice Plant", International Rice Research Institute, Lesson 2, http://www.knowledgebank.irri.org/ericeproduction/0.2, 2007, 2 pages.
Verreynne et al., "Citrus Fruit Reduce Summer and Fall Vegetative Shoot Growth and Return Bloom", Proceedings ofthe International Society of Citriculture, vol. II., Feb. 2004., pp. 520-524.
Verreynne et al., "The Effect of Crop Load on Budbreak Influences Return Bloom in Alternate Bearing 'Pixie' Mandarin", J. Amer. Soc. Hort. Sci., vol. 134, No. 3, 2009, pp. 299-307.
Verreynne, "The Mechanism and Underlying Physiology Perpetuating Alternate Bearing in 'Pixie' Mandarin (Citrus *Reticulata blanco*)", University of California Riverside, Jun. 2005, 214 pages.
Woo et al., "Flavonoids: From Cell Cycle Regulation to Biotechnology", Biotechnology Letters, vol. 27, 2005, pp. 365-374.
Extended European Search Report received for European Patent Application No. 10844271.6, mailed on Jul. 8, 2013, 6 pages.
International Preliminary Report on Patentability received for PCT Patent Application No. PCT/US2010/062268, mailed on Jul. 12, 2012, 5 pages.
International Preliminary Examination Report on received for PCT Patent Application No. PCT/US2010/062267, mailed on Jul. 12, 2012, 6 Pages.
International Search Report and Written Opinion received for PCT Patent Application No. PCT/US2010/062267, mailed on Sep. 20, 2011, 9 pages.
International Search Report and Written Opinion received for PCT Patent Application No. PCT/US2010/062268, mailed on Sep. 20, 2011, 8 pages.
"Fertilizers and Use", Food and Agriculture Organization of the United Nations, International Fertilizer Industry Association (IFA), 4th edition, 2002.
"Humic—Plant Nutrition", Product Catalogue—Amino acids. Datasheet of Briohumic, available at <http://www.humic.es/aminoacidos/briohumic.pdf>, Oct. 2007.
Bukovac et al., "Modifying Alternate Bearing of Spur-Type 'Delicious' Apple with Ethephon", Hortscience, vol. 41, No. 7, 2006, pp. 1606-1611.
Ito et al., "Studies on the Physiological Responses of Crop Plants Following Application of Exogenous Nucleic Acid Components. I. Effect of Exogeneous Nucleic Acid Components on the Germination of Seeds and the Growth of Seeding During the Early Stages of the Rice", Plant, *Oryza stativa*, Tokyo Nogyo Daigaku Nogaku Shuho, vol. 20, No. 1, 1975, pp. 35-42. Japanese with English abstract.
Rao et al., "Enhancement of Polyribosome Formation by Gibberellic Acid and 3',5'-Adenosine Monophosphate in Barley Embryos", Biochemical and Biophysical Research Communications, vol. 62, No. 1, 1975, pp. 25-30.
Spinelli et al., "Perspectives on the use of a Seaweed Extract to Moderate the Negative Effects of Alternate Bearing in Apple Trees", Journal of Horticultural Science & Biotechnology, 2009, pp. 131-137.
Extended European Search Report (includes Supplementary European Search Report and Search Opinion) received for European Patent Application No. 10844272.4, mailed on Apr. 8, 2014, 8 pages.

* cited by examiner

Navel Orange

Hass Avocado

USE OF 9-BETA-D-ADENOSINE TO INCREASE CROP PRODUCTION

CROSS-REFERENCE TO RELATED APPLICATIONS

This application is a continuation of U.S. application Ser. No. 14/503,276, filed Sep. 30, 2014, now abandoned, which is a continuation of U.S. application Ser. No. 13/519,889, now U.S. Pat. No. 8,846,572, which is a U.S. national stage application of International Application No. PCT/US2010/062267, filed Dec. 28, 2010, which claims the benefit under 35 USC 119(e) of U.S. Provisional Patent Application No. 61/290,473, filed Dec. 28, 2009, each of which is incorporated herein by reference in its entirety for all purposes.

FIELD

Described are compositions and methods to increase bud break in order to increase aspects of one or both of plant vegetative and reproductive growth, by use of a natural metabolite. In particular, the present disclosure provides a natural metabolite either alone or as part of a fertilizer blend to increase crop production. Additionally the present disclosure provides a natural metabolite in combination with one or both of a plant growth regulator and a bio stimulant to increase crop production.

BACKGROUND

Increasing world populations and dwindling productive farm land place increasing demands on agricultural efficiency. The sustainability of agriculture demands that production per unit area of land be increased in a cost-effective manner. It has long been the goal of growers to be able to manipulate the vegetative and reproductive growth of plants to increase the quantity and quality of crops. Cultivars of vegetable, fruit, nut, grain, forage and ornamental crops are no exception. Total yield is expressed as a function of quantity and mass as the product of organ (e.g., root, stem, leaf, flower, seed and fruit) or plant number multiplied by organ or plant weight. Thus, an increase in total crop yield may result from an increase in quantity, an increase in mass, or a combination of the two. As growers strive to increase profitability of their farm lands, quantity and size has become increasingly important. This is increasingly important in the production of fruit and nut crops. Accordingly, since consumers tend to prefer large size fruit and nuts, they are commercially more valuable than small size fruit and nuts.

Total yield of vegetable, fruit, nut, grain, forage and ornamental crops is affected by many factors. For instance, fruit quantity is dependent on flower number and the number of branches capable of bearing flowers, while fruit size is dependent on the number of fruit set. Seed production influences both the number of fruit set and fruit size. Fruit size is also influenced by the number of leaves exporting the products of photosynthesis to the fruit. Root, tuber and bulb crops are similarly affected by the number of leaves exporting photosynthate to the below ground portions of the plant. Above and below ground parts of the plant produce hormones that further affect plant growth and crop yield. Root development, nutrient uptake, water availability, climate and stress (abiotic and biotic) all affect photosynthesis and plant metabolism and hence fruit size. Additionally, all aspects of production are affected by agricultural practices such as pruning, fertilization, irrigation and use of nutritional supplements and plant growth regulators.

At the present time, plant growth regulators (PGRs) are one of the most powerful tools available for manipulating the vegetative and reproductive growth of crop plants. For a wide variety of annual, biennial and perennial crops, PGRs have been used to solve production problems. For example, PGRs have been used successfully as foliar sprays to increase flowering, synchronize bloom, or change the time of flowering to avoid adverse climatic conditions or to shift harvest to a time when the market is more economically favorable. Foliar-applied PGRs are routinely used to improve fruit set, reduce June drop or to prevent pre-harvest drop to increase yield. PGR sprays are applied to increase fruit size directly by stimulating cell division. Application of a PGR that reduces the number of flowers formed or promotes flower or fruit abscission increases fruit size indirectly by decreasing fruit number. PGRs have been used as both pre- and post-harvest treatments to hasten or slow the ripening process, color development, and maturation of specific tissues to improve the quality of the product sold in the market. An emerging use of PGRs is for overcoming the adverse effects of abiotic stresses. Surprisingly, these successes have been achieved with a modest number of commercial PGRs that are members of or impact the synthesis of one of five classic groups: auxins, cytokinins, gibberellins, abscisic acid and ethylene.

However, as many PGRs are synthetic chemical compounds that mimic the effects of natural plant hormones, they are subject to regulation under the Federal Insecticide, Fungicide, and Rodenticide Act, administered by the United States Environmental Protection Agency. In addition to the regulatory hurdles faced by PGRs, their use is not favorably received by a growing segment of consumers who prefer organic produce. As such, what the art needs are compositions and methods that employ natural compounds to increase crop production.

SUMMARY

Described are compositions and methods to increase bud break in order to increase aspects of one or both of plant vegetative and reproductive growth, by use of a natural metabolite. In particular, the present disclosure provides a natural metabolite either alone or as part of a fertilizer blend to increase crop production. Additionally the present disclosure provides a natural metabolite in combination with one or both of a plant growth regulator and a biostimulant to increase crop production. The present disclosure further provides a natural metabolite that, depending on use, might itself be labeled a nutritional supplement, a biostimulant or a plant growth regulator.

The present disclosure provides methods of increasing crop production, comprising administering to a crop plant a composition comprising an effective amount of a purified natural compound to increase the crop production of the crop plant, wherein the natural compound is selected from the group consisting of adenosine, an adenosine phosphate, inosine, an inosine phosphate, adenine, hypoxanthine, xanthine, and combinations thereof. In other embodiments, the natural compound is selected from the group consisting of uridine, uridine monophosphate, uridine diphosphate, uridine triphosphate, and uracil. In some preferred embodiments, the natural compound comprises 9-beta-D-adenosine. In some preferred embodiments, the natural compound comprises one or more of the group consisting of adenosine monophosphate, adenosine diphosphate, adenosine triphosphate, inosine, inosine monophosphate, inosine diphosphate, inosine triphosphate, adenine, hypoxanthine, and xanthine. In some preferred embodiments, the composition further comprises one or more of a fertilizer, a plant growth regulator, a biostimulant, and a bioactive agent (e.g., insecticide, fungicide, bactericide, and/or acaricide). In a subset of these embodiments, the plant growth regulator comprises one or more of TIBA, IPA, and 6-BA. In other embodiments, the plant growth regulator is provided in Vermicompost tea. In some embodiments, the fertilizer is selected from the group consisting of nitrogen, potassium, magnesium, phosphorus, calcium, sulfur, iron, boron, chlorine, manganese, zinc, copper, molybdenum, nickel, cobalt, silicon, selenium, and combinations thereof. The present disclosure provides methods in which the crop plant is a perennial fruit plant. In some preferred embodiments, the perennial fruit plant is selected from the group consisting of apple, apricot, avocado, citrus (e.g., orange, lemon, grapefruit, tangerine, lime and citron), peach, pear, pecan, pistachio, and plum. In some embodiments, the composition is administered at one or more of the following times: (i) at 10% anthesis, (ii) at full bloom, (iii) 30 days after 75% petal fall, (iv) at maximum peel thickness of the fruit, and (v) greater than 60 days, preferably greater than 75, 90, 105, 120, 135, 150, 175 or 180 days (from 75 to 180 days) before fruit harvest. In some embodiments, the crop plant is an annual crop plant. In a subset of these embodiments, the annual crop plant is selected from the group consisting of celery, spinach, and tomato. In some preferred embodiments, the composition is administered, one, two, three, four, five, six or seven times per week. The present disclosure provides methods in which the composition is administered by a technique selected from the group consisting of foliar spray, irrigation, and trunk injection. In some embodiments, the increased crop production comprises an increase in reproductive growth. In a subset of these embodiments, the increase in reproductive growth comprises an increase of one or more of the group consisting of number of fruiting shoots, number of fruit, fruit size, and total yield of fruit (per plant or per plot basis). In some preferred embodiments, the increase in reproductive growth comprises an increase in yield of commercially valuable large fruit (yield of mammoth, jumbo and large fruit) on a per plant or per plot basis. In some embodiments the increase in fruit size comprises one or more of the following: an increase in average fruit diameter per crop plant (of at least 10%, 20%, 30%, 40%, 50%, 60%, 70%, 80%, or 90%, or between 10 to 90% that of an untreated crop plant); an increase in average fruit weight per crop plant (of at least 10%, 20%, 30%, 40%, 50%, 60%, 70%, 80%, or 90%, or between 10 to 90% that of an untreated crop plant); and an increase in total fruit weight per crop plant (of at least 10%, 20%, 30%, 40%, 50%, 60%, 70%, 80%, or 90%, or between 10 to 90% that of an untreated crop plant). In some embodiments, the increased crop production comprises an increase in vegetative growth, wherein the increase in vegetative growth comprises an increase in one or both of number of leaves and number of vegetative shoots (per plant or per plot basis). In some embodiments, the adenosine is administered as a biostimulant, a nutritional supplement, or a plant growth regulator.

Additionally, the present disclosure provides a composition comprising: (i) a purified natural compound, and (ii) a fertilizer, wherein the natural compound is selected from the group consisting of adenosine, an adenosine phosphate, inosine, an inosine phosphate, adenine, hypoxanthine, xanthine, and combinations thereof. In other embodiments, the natural compound is selected from the group consisting of uridine, uridine monophosphate, uridine diphosphate, uridine triphosphate, and uracil. In some preferred embodiments, the natural compound comprises 9-beta-D-adenosine. In some preferred embodiments, the natural compound comprises one or more of the group consisting of adenosine monophosphate, adenosine diphosphate, adenosine triphosphate, inosine, inosine monophosphate, inosine diphosphate, inosine triphosphate, adenine, hypoxanthine, and xanthine. In some embodiments, the fertilizer is selected from the group consisting of nitrogen, potassium, magnesium, phosphorus, calcium, sulfur, iron, boron, chlorine, manganese, zinc, copper, molybdenum, nickel, cobalt, selenium, silicon and combinations thereof. Also, the present disclosure provides compositions which further comprise a bioactive agent (e.g., insecticide, fungicide, bactericide, and/or acaricide).

BRIEF DESCRIPTION OF THE DRAWINGS

FIG. 1 is based on 25-year-old 'Washington' navel orange trees on Troyer citrange rootstock at Riverside, Calif.

FIG. 2 is based on San Diego—Riverside environmental conditions.

Figure 1:
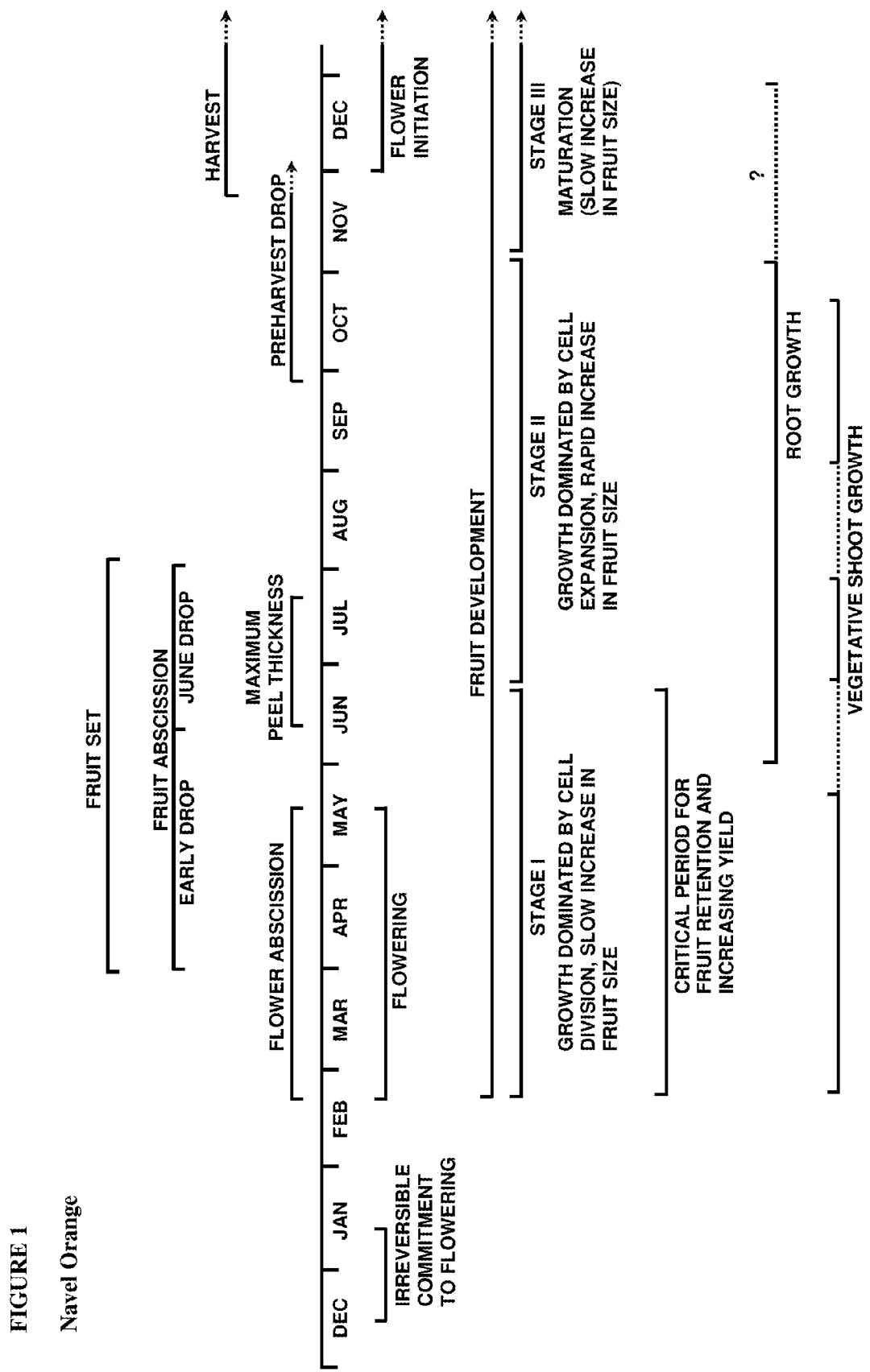
FIG. 1 is a timeline depicting the flowering, fruit set and fruit development of the Navel orange over a one-year period. Trees transition from vegetative to reproductive (floral) development from late November through January, with irreversible commitment to flowering (determinancy) occurring between mid-December and mid-January. Flowering and flower abscission may occur between February and mid-May or June. Fruit set may occur between February and July. Fruit abscission may occur between April and August. Fruit development unfolds in three stages. During Stage I, which may occur between February and July, fruit size slowly increases. The end of Stage one is marked by maximum thickness of the peel and has been experimentally shown to occur between approximately June 10 and July 26 for both navel and Valencia orange and mandarins from as far south as Irvine Calif. north to Madera Calif., occurring earlier within this period for cultivars with a thinner peel, i.e., mandarin<Valencia<navel and earlier within a cultivar during an on-crop year than an off-crop year. During Stage II, which may occur between June and November, fruit size rapidly increases. During Stage III, which may occur between November and January of the following year, is a maturation stage wherein the increase in fruit size slows down again. Stages I and II (early fruit drop and June fruit drop period, respectively) are the critical period for fruit retention and increasing yield. The end of Stage I through Stage II is the critical period for increasing fruit size. Pre-harvest may occur between September and December, while harvest may occur from December until as late as June of the following year.
Figure 2:
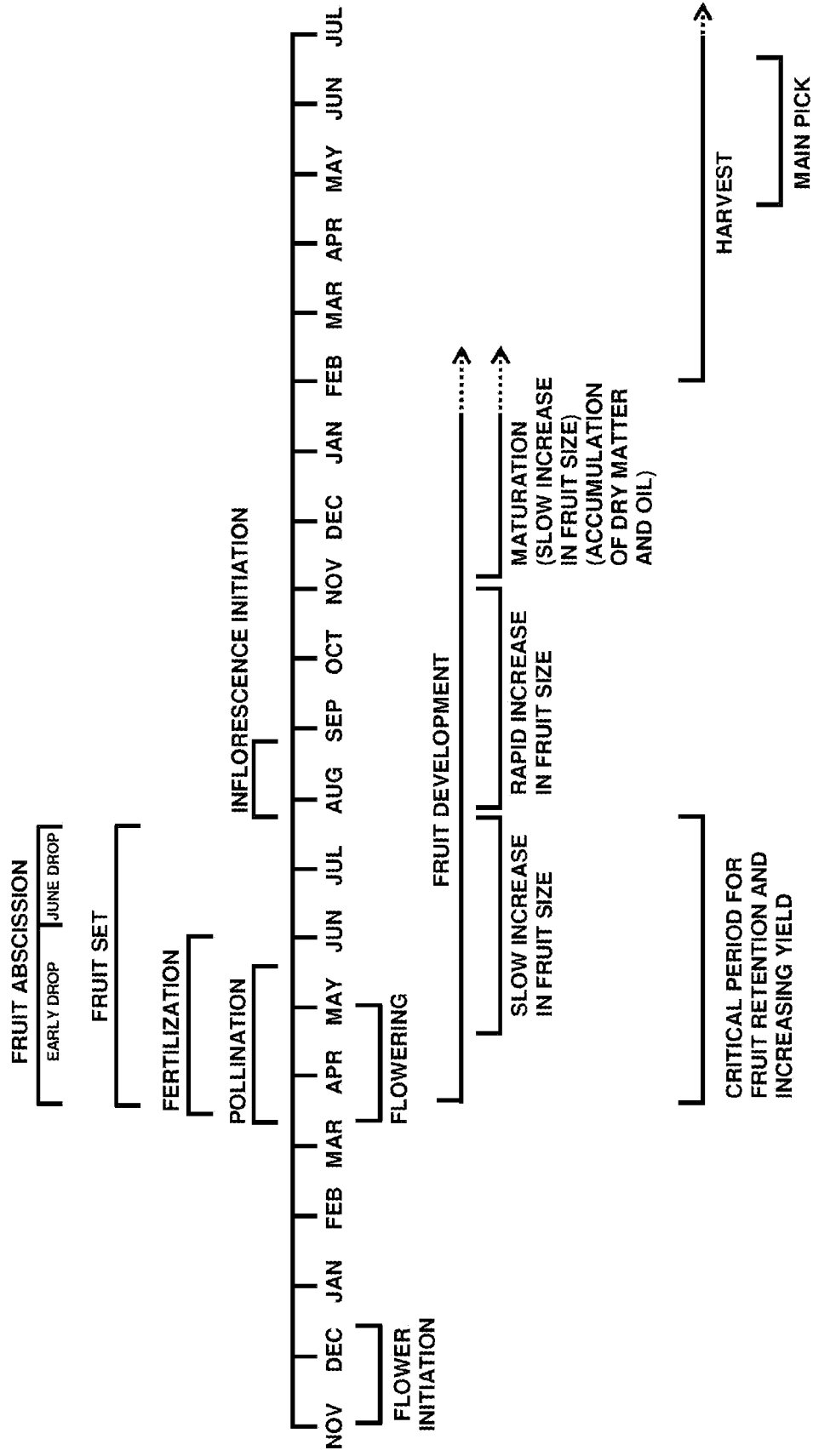
FIG. 2 is a timeline depicting the flowering, fruit set and fruit development of the 'Hass' avocado in California over approximately a 1.5-year period. The 'Hass' avocado in California transitions from vegetative to reproduction development (inflorescence initiation) at the end of July beginning of August. Flower initiation may occur between November until January of the following year. Flowering may occur between March and May. Pollination and fertilization may occur between March and June. Fruit set may occur between March and mid-June to early July. Early fruit drop may occur between March and mid-June to early July; June drop occurs from mid-June to early July through August. Fruit development unfolds in three stages. During Stage I, which may occur between April and mid-June-early July, fruit size slowly increases. During Stage II, which may occur between mid-June-early July through November, fruit size rapidly increases. During Stage III, the fruit continue to undergo cell division and to accumulate dry matter and oil content as part of maturation, which continues through harvest (20.8% dry matter content is legal maturity) the following year. The critical period for fruit retention and increasing yield is between March and August. The critical period for increasing fruit size is mid-June to early July through November and again late March to early April through to harvest the following year. Harvest may occur between February until fall, wherein the main pick occurs between May and July.

Tomato fruit growth also proceeds through the same three stages of fruit development. In addition, the three stages of tomato fruit development have the same associated fruit drop periods: Stage I of fruit development, early fruit drop; Stage II of fruit development, June fruit drop period; and Stage III of fruit development, pre-harvest fruit drop.

All crops (annual, biennial or perennial; vegetable, fruit, nut, grain, forage or ornamental) have stages of phenology that can be targeted for treatment with foliar-, soil- or irrigation-applied, and in the case of tree crops, trunk injected, nutritional supplements, fertilizers or plant growth regulators to increase the number, size and total yield of the marketable crop (organ or entire plant).

DEFINITIONS

To ensure a complete understanding of this disclosure, the following definitions are provided:

The term "natural metabolite" as used herein refers to a substance existing in nature that is involved in metabolism (e.g., product of or necessary for metabolism). In some embodiments, the natural metabolite is adenosine. Similarly, the term "natural compound" as used herein refers to a substance existing in nature, albeit whether the isolated compound is produced biologically or chemically. For the sake of simplicity, the terms "natural metabolite" and "natural compound" are used interchangeably herein. In some preferred embodiments the natural compound is: a purine nucleoside (e.g., adenosine, inosine); a monophosphate, diphosphate or triphosphate of a purine nucleoside (e.g., AMP, ADP, ATP, IMP, IDP, ITP); or a purine base (e.g., adenine, hypoxanthine, xanthine). In preferred embodiments, the natural metabolite comprises adenosine. In preferred embodiments, the purine nucleoside comprises or consists essentially of the D stereoisomer (e.g., 9-beta-D-adenosine, 9-beta-D-inosine).

As used herein, the term "purified" refers to a metabolite (e.g., adenosine or the like) that is removed from its natural environment (e.g., isolated or separated). "Purified" compounds are at least 50% free, preferably 75% free, more preferably at least 90% free, and most preferably at least 95% (e.g., 95%, 96%, 97%, 98%, or 99%) free from other components with which they are naturally associated.

The term "nutritional supplement" as used herein refers to a composition comprising one or more basal metabolites needed for normal growth of plants, and which are in a form readily useable by plants. In some preferred embodiments, the nutritional supplement comprises the natural metabolite adenosine. In some preferred embodiments, the adenosine is 9-beta-D-adenosine. In other preferred embodiments the nutritional supplment comprises the natural metabolite adensoine in combination with pyrimidine nucleosides, bases or nucleotides, amino acids, organic acids, anti-oxidants, sugars and vitamins, enzyme cofactors.

The term "fertilizer" as used herein refers to one or more of the 17 nutritional elements essential for plant and fruit growth and seed production, and any of several elements shown to be beneficial for plant growth. Fertilizers may be added to the soil of crops, as liquids or solids, for uptake by plant roots (e.g. soil-applied, irrigation-applied) or applied to the canopy of the plant for uptake through leaves, inflorescences, flowers, fruit, and buds. Fertilizers may be organic (i.e. composed of decayed plant or animal matter) or inorganic (i.e. composed of single or multiple chemicals and minerals). Fertilizers may include, in varying proportions, the essential elements: nitrogen, phosphorus, potassium, calcium, sulfur, magnesium, boron, chlorine, manganese, iron, zinc, copper, molybdenum, and nickel. Fertilizers may also include the beneficial elements cobalt, silicon, selenium, and chromium. Urea (e.g. low-biuret urea) is an example of a preferred nitrogen fertilizer.

The terms "plant growth regulator" and "PGR" as used herein refer to a synthetic chemical analog of a naturally occurring plant hormone that is applied to mimic the effects of plant hormones. The naturally occurring plant hormones generally fall under one of five classes: auxin, gibberellin (GA), cytokinin, ethylene, and abscisic acid (ABA). Plant growth regulators include but are not limited to 2,3,5-triiodobenzoic acid (TIBA); 9-hydroxyflorene-9-carboxylic acid (HFCA); 2-(4-chlorophenoxy)-2-methylpropionic acid (clofibric acid); 4-chlorophenoxyacetic acid (4-CPA); 2,4-dichlorophenoxyacetic acid (2,4-D); 2,4,5-trichlorophenoxyacetic acid (2,4,5-T); 3,5,6-trichloro-2-pyridyloxyacetic acid (3,5,6-TPA); 4-(2,4-dichlorophenoxy)butyric acid (2,4-DB); tris[2-(2,4-dichlorophenoxy)ethyl]phosphite (2,4-DEP); 2-(2,4-dichlorophenoxy)propionic acid (dichlorprop); 2-(2,4,5-trichlorophenoxy)propionic acid (fenoprop); 1-naphthaleneacetic acid (NAA); indole-3-butyric acid (IBA); indole-3-acetic acid (IAA); 4-chloroindole-3-acetic acid (4-CI-IAA); 2-phenylacetic acid (PAA); 2-methoxy-3,6-dichlorobenzoic acid (dicamba); 4-amino-3,5,6-trichloropicolinic acid (tordon or picloram); α-(p-Chlorophenoxy)isobutyric acid (PCIB); 1-naphthol; (2-naphthyloxy)acetic acid; potassium naphthenate; sodium naphthenate; N-(3-methylbut-2-enyl)-1H-purin-6-amine (2iP); N-benzyl-1H-purin-6-amine (benzyladenine and its riiboside); N-furfuryl-1H-purin-6-amine (kinetin); (E)-2-methyl-4-(9H-purin-6-ylamino)but-2-en-1-ol (zeatin); 6-benzylaminopurine (6BA); isopentenyladenine and its riboside; zeatin and its riboside; 1-(2-chloro-4-pyridynl)-3-phenyluea (CPPU), forchlorfenuron, and other synthetic diphenylurea-type cytokinins; cis, trans-abscisic acid; S-(+)-abscisic acid; (S)-5-(1-hydroxy-2,6,6-trimethyl-4-oxo-1-cyclohex-2-enyl)-3-methyl-penta-(2Z,4E)-dienoic acid; gibberellic acids ($GA_3$, $GA_4$, $GA_7$, $GA_{4+7}$, $GA_9$, $GA_{4,7,9}$, $GA_1$); fluridone (1-methyl-3-phenyl-5-[3-trifluromethyl(phenyl)]-4-(1H)-pyridinone); abamine; 1-butanol; 1-methylcyclopropene (MCP); amnioethoxyvinylglycine; ethephon; and ethrel.

The term "biostimulant" as used herein refers to a compound or composition that is neither a fertilizer nor pesticide, but which when applied to a plant will enhance the health and growth of a plant. The term biostimulant encompasses but is not limited to pyrimidine nucleotides, nucleosides and bases, amino acids, organic acids, sugars, vitamins, enzyme cofactors, anti-oxidants, humic acid, fulvic acid, kelp (seaweed), and compost teas.

The term "crop production" as used herein refers to aspects of one or both of vegetative growth (shoots, leaves) and reproductive growth (flowers, fruits, seeds). As such an increase in crop production encompasses an increase in one or both of the quantity and size of the organs of a plant, including but not limited to fruit, seeds/nuts, flowers, inflorescences, shoots, and leaves. The term "quantity" as used herein refers to an increase in the number of plant organs (e.g., number of vegetative shoots, number of leaves, number of reproductive [floral] shoots, number of inflorescences, number of flowers, number of fruit). The term "size" as used herein refers to the weight, length, area, diameter, circumference or volume of a plant organ, while the term "quantity" as used herein refers to number of plant organs. An increase in size encompasses an increase in one or more of: plant size (e.g., height, width); shoot size (e.g., length, diameter, circumference); leaf size (e.g., length, width, area); and fruit size (e.g., diameter, circumference, volume, weight). In preferred embodiments, the increase in crop production is a net increase of at least 10%, 20%, 30%, 40%, 50%, 75%, 85%, 95%, 100%, 150%, 200% in fruit production (e.g., number of fruit [total, large, or commercially valuable] per crop plant, weight of fruit [total, large, or commercially valuable] per crop plant, or total yield of fruit per crop plant) as compared to the respective values of untreated control plants. Crop production is generally expressed in: total kilograms of fruit per crop plant, average kilogram per fruit per crop plant, total number of fruit per crop plant, average number of fruit per crop plant, average millimeters in diameter per fruit, or in average grams per fruit.

The term "total yield" as used herein refers to the product of size multiplied by quantity of a plant organ. In preferred embodiments, the increase in total yield is a net increase of at least 10%, 20%, 30%, 40%, 50%, 75%, 100%, 150%, 200%, 250%, 300%, 350%, 400%, or 500% of the total yield of one or both of vegetative and reproductive growth as compared to the value of untreated control plants.

The term "administer" as used herein refers to various ways in which a crop plant receives the compositions described herein (e.g., nutritional supplements, fertilizers, plant growth regulators, and combinations thereof). Methods of administration include, but are not limited to foliar spray, irrigation, soil application, soil injection, trunk injection (including branch injection), and trunk paints (including branch paints). Foliar spraying, a technique of feeding plants, involves directly applying the composition in liquid form to the canopy of the plant. Whereas leaves are typically the target of such applications, alternatively buds, inflorescences, flowers, and fruit might be the target of foliar sprays alone or in addition to leaves. In contrast, irrigation involves directly administering the composition to the root zone for uptake by the plant roots. Trunk injection involves directly administering the composition to the plant trunk or branch. As known in the art, trunk injection is a way to treat many different insect and disease problems, as well as nutrient deficiencies, in an efficient and environmentally friendly way. Also, some trees are too large to spray, in areas too close to houses, parks, water courses, or other environmentally sensitive areas where spraying is not a viable option, or the root system may be inaccessible for soil systemic treatments, making trunk injection the best or only option available in such cases.

The term "effective amount" as used herein refers to that amount of a substance that is necessary to produce a desired effect. In some embodiments, an effective amount of adenosine is that amount of adenosine that increases fruit size (circumference, weight and/or volume) when administered in a suitable manner to a crop plant (e.g., appropriate formulation of adenosine applied at an appropriate time given the stage of fruit development). In some embodiments, an effective amount of adenosine is that amount of adenosine that increases one or both of shoot number and fruit number when administered in a suitable manner to a crop plant (e.g., appropriate formulation of adenosine applied at an appropriate time given the stage of fruit development). Typically, an effective amount of adenosine administered to a crop plant by foliar spray is between about 0.023 kg/acre to 0.189 kg/acre (e.g., 25 mg/L applied in 950 L of water per acre to 100 mg/L applied in 1900 L of water per acre). Typically, an effective amount of adenosine administered to a crop plant by irrigation is a total of 0.35 µg to 35 µg per plant over a 3-month growing period or 1.4 mg/4000 plants/acre 140 mg/4000/acre through a 3-month growing season. Typically, an effective amount of adenosine administered to a crop plant by trunk injection is between 250 mg to 2500 mg per tree per application. At a density of 200 trees per acre and a dose of 1 gram per tree, 0.2 kg adenosine per acre is used applied in an exemplary application.

The terms "bud break" and "budburst" as used herein refer to the phenomenon whereby a dormant bud resumes growth, resulting in enhanced vegetative or reproductive shoot growth. A dormant bud refers to bud that is capable of growth but which is not growing due to external or endogenous factors. However, not all shoots develop from a dormant bud. Buds can develop de novo contemporaneously with the main axis of the shoot. The phenomenon whereby these buds are formed and grow to increase vegetative and reproductive shoot growth is also "bud break" and "budburst".

The term "maximum peel thickness" as used herein refers to the period at the end of the cell division stage of fruit (e.g. citrus) development.

The term "anthesis" as used herein refers to a period during which a flower is opening (e.g., undergoing anther dehiscence). The term 10% anthesis, 60% anthesis etc, refers to percentage of flowers that have undergone anthesis in the southwest quadrant of the tree.

The term "full bloom" as used herein refers to a period in a plant's bloom cycle in which ~50% of the flower buds are open.

The term "petal fall" as used herein refers to the period in which 75% of flowers have undergone petal drop in the northeast quadrant of the tree.

The term "canopy" as used herein refers to components of a plant that are above the level of the soil, with the exception of the trunk. As such, the term canopy encompasses branches, leaves, inflorescences, flowers, buds and fruit.

The term "crop plant" as used herein generally refers to cereal, legumes, forage crops, stem and leaf crops, tuber, corm, bulb and root crops, fruit and seed vegetables, fruit and nut crops, beverage crops, oil, fat and wax crops, spices, perfumes and flavorings, and ornamentals, forest and fiber crops. Crop plants include, but are not limited to rice, wheat, corn, barley, oats, sorghum, rye, millet, soybean, peanut, beans, broad bean, pea, chickpea or garbanzo, black eyed pea, lentil, pigeon pea, guar, alfalfa, clover, bird's foot trefoil, vetch, sweet clover, lespedeza, lupine, sorghum-sudan, Kentucky bluegrass, brome grass, timothy, orchard grass, fescua, Bermuda grass, dallies grass, bahia grass, ryegrass, bent grass, sugar cane, artichoke, asparagus, broccoli, brussels sprouts, cabbage, celery, chard, Chinese cabbage, collards, endive, kohlrabi, lettuce, parsley, rhubarb, spinach, potato, cassava, sweet potato, beets, taro, carrot, horseradish, Jerusalem artichoke, onion, parsnip, radish, rutabaga, salsify, turnip, yam, tomato, eggplant, curcurbits, okra, pepper, citrus (including sweet orange, mandarin orange, lemon, limes, grapefruit), grape, banana, apple, stone fruits (e.g. apricot, nectarines, peach, plum), blueberry, raspberry, blackberry, mulberry, brambles, cranberry, currant, pear, avocado, cashew, coconut, date, fig, guava, litchi, maracuja, mango, olive, *papaya*, pineapple, pomegranate, almond, brazil nut, filberts, macadamia, pecan, pistachio, walnuts, sunflower, coffee, tea, cacao, cola, hops, safflower, coconut, African oil palm, castor bean, rape, sesame, sunflower, linseed, tung, soybean, carnauba, candelilla, jojoba, black pepper, cinnamon, clove, vanilla, mint, oregano, allspice, anise, *angelica* oil, mustard, sage, ginger, rose oil, bergamot, camphor, *cananga*, citronella grass, *eucalyptus*, geranium oil, *lavandula*, rosemary, thyme, turpentine, cotton, flax, hemp, Christmas trees (various conifers), ornamental evergreens, rose, *chrysanthemum*, carnation, iris, azalea and *rhododendron*.

The term "crop plant" encompasses annuals, biennials, and perennials. A perennial plant lives for more than two years. In contrast, an annual plant germinates, flowers, and dies in one year; while a biennial plant completes its life cycle in two years. The embodiments in the present disclosure apply to all crop plants.

DETAILED DESCRIPTION

Described are compositions and methods to increase aspects of one or both of plant vegetative and reproductive growth, by use of a natural metabolite. In particular, the present disclosure provides a natural metabolite either alone or as part of a fertilizer blend to increase crop production. Additionally the present disclosure provides a natural metabolite in combination with one or both of a plant growth regulator and a biostimulant to increase crop production. In some embodiments, the natural metabolite comprises one or more of adenosine, adenosine phosphates (AMP, ADP, ATP) inosine, inosine phosphates (IMP, IDP, ITP) adenine, hypoxanthine, and xanthine. In some preferred embodiments the natural metabolite comprises adenosine. In some preferred embodiments, adenosine comprises or consists essentially of the D stereoisomer (e.g., 9-beta-D-adenosine). In the detailed description below, exemplary methods and compositions comprising 9-beta-D-adenosine are provided. However, the present disclosure is not so limited and as such other suitable compositions and methods for increasing crop production comprise adenosine phosphates, inosine, inosine phosphates, adenine, hypoxanthine and xanthine in addition to or instead of adenosine. In some preferred embodiments, inosine comprises or consists essentially of the D-sterioisomer (e.g., 9-beta-D-inosine).

I. Methods of Increasing Crop Production

The present disclosure provides methods for increasing crop production, which involves increasing bud break resulting in increased production of one or both of vegetative and reproductive shoot numbers by administering to the crop plant a composition comprising a natural metabolite. In some embodiments, the natural metabolite comprises one or more of adenosine, adenosine phosphates (AMP, ADP, ATP) inosine, inosine phosphates (IMP, IDP, ITP) adenine, hypoxanthine, and xanthine. In some embodiments the composition is intended for use as a nutritional supplement, while in other embodiments, the composition is intended for use as a plant growth regulator or as a biostimulant. The present disclosure is compatible with the standard practices of the tomato, pepper, strawberry, ornamental vegetative and flowering herbaceous or woody plants, and other vegetable, grains, spice, forage and annual, biennial and perennial fruit and seed crop industries.

Previous investigators have shown that administration of AMP to cotton seed was effective in increasing seed germination (U.S. Pat. No. 4,209,316). In contrast, the present disclosure does not increase crop production as a consequence of enhancing germination. Moreover in preferred embodiments, the present disclosure comprises the administration of adenosine, as opposed to AMP.

The use of 1-tricontanol or 9-beta-L-adenosine has been reported to improve the quality of a harvested plant part (U.S. Pat. No. 5,217,738). In some instances this involved increasing the sugar to acid ratio of a harvested fruit or vegetable. In further reports, 9-beta-L-adenosine was administered to seedlings to increase dry weight or to plants once within 60 days of fruit or vegetable harvest to improve firmness or storage stability (U.S. Pat. Nos. 5,009,698 and 5,234,898). In contrast, the present disclosure involves the administration of a composition comprising a natural metabolite (adenosine or the like, preferably 9-beta-D-adenosine) to a crop plant prior to harvest of the fruit or vegetable. Moreover, the present disclosure involves increasing crop production by increasing bud break, as opposed to generally increasing plant growth (e.g., vegetative shoot length). In preferred embodiments, the present disclosure involves repeated administration of the natural metabolite and/or administration at a defined stage(s) of plant growth. As such the compositions and methods of the present disclosure differ significantly from the patents referred to above.

A. Methods of Increasing Tomato Production

Exemplary methods for increasing the production of tomatoes are provided in Example 1 and briefly summarized below. In some embodiments, adenosine is applied to tomatoes through the irrigation in a sufficient amount of water to move the material into the root zone approximately once every day, once every other day, once every 7 days, or once every 10 days to provide 0.35 µg to 35 µg per plant over a 3-month growing period or 1.4 mg/4000 plants/acre 140 mg/4000/acre through a 3-month growing season. In further embodiments, adenosine is applied as a foliar spray once every 7 to 10 days to provide 0.35 µg per plant or 35 µg per plant over a 3-month growing period or 1.4 mg/4000 plants/acre 140 mg/4000/acre through a 3-month growing season. In additional embodiments, adenosine is applied at key stages of plant phenology (e.g., just prior to the initiation of flowering, during full bloom, during fruit set [Stage I of fruit development], during the period of exponential increase in fruit size [(Stage II of fruit development and also the June fruit drop period] or during fruit set [Stage I of fruit development] and again just prior to or during the period of exponential increase in fruit size (Stage II of fruit development and also the June fruit drop period) at 2.5 mg/L or 50 mg/L or 100 mg/L in sufficient gallons of water per acre to provide good canopy coverage. The methods of the present disclosure for increasing tomato production through administration of a composition comprising adenosine are expected to compare favorably to untreated controls, as well as standard available practices (e.g., vermicompost tea applied at 3 gallons/acre, 3 times/month over the 3-month growing season).

B. Methods of Increasing Mandarin Production

Exemplary methods for increasing production of citrus are provided in Example 2 and briefly summarized below. In some embodiments, the methods involve administering a composition comprising adenosine by foliar spray to mandarin trees. Suitable methods involving canopy application are as follows: (1) adenosine (25 mg/L) administered at maximum peel thickness; (2) adenosine (25 mg/L) administered when fruit are 17-20 mm in diameter; (3) adenosine (50 mg/L) administered when fruit are 17-20 mm in diameter; (4) adenosine (50 mg/L) administered at maximum peel thickness; (5) adenosine (100 mg/L) administered when fruit are 17-20 mm in diameter; (6) adenosine (100 mg/L) administered at maximum peel thickness; (7) adenosine (50 mg/L) administered at 75% petal fall) and (8) adenosine (50 mg/L) administered at 75% petal fall and at maximum peel thickness. The treatments can be applied in 100 to 500 gallons per acre. Unless otherwise stated, the exemplary treatments are applied in 250 gallons of water per acre. Thus adenosine is applied in amounts from about 18.93-23.66 g per acre to about 75.71-94.63 g per acre. There are 15 individual tree replicates per treatment in test methods. At harvest, fruit production is assessed (kg fruit per tree, fruit number per tree and fruit quality).

The methods of the present disclosure for increasing citrus production through administration of a composition comprising adenosine are expected to compare favorably to untreated controls, as well as standard available practices. In particular an increase in citrus production is achievable by increasing fruit retention, and thus fruit number with or without an effect on fruit size. Standard available practices for mandarin trees are as follows: (1) $GA_3$ (PROGIBB® 4% from Valent Biosciences Corp.) at 1-8 fluid oz per 100 gallons of water, using a sufficient number of gallons for good coverage; 1-2 applications from 50% petal fall to 3 weeks after petal fall of mandarins and mandarin hybrids; (2) 2,4-D (CITRUSFIX® from AmVac Corp.) 0.67 oz (3.34 lbs 2,4-D isopropylester per gallon) per 100 gallons of water at 500 gallons per acre 21 to 35 days after 75% petal fall of mandarins and mandarin hybrids; and (3) 1% low-biuret urea applied at maximum peel thickness. PROGIBB® must be used with caution as it may result in more fruit set than is desirable, resulting in a reduction in final fruit size and leaf drop in trees under stress. Adenosine in a preferred embodiment does not require this caution and its efficacy in increasing production of commercially valuable fruit is not as sensitive to crop load (alternate bearing) as that of methods comprising administration of $GA_3$. Similarly, CITRUSFIX® must be used with caution as it may cause fruit dryness. This is particularly relevant to 'Nules' and other cultivars that tend to be dry or granulated, and cannot be used on trees less than 6 years old and cannot be used during a flush of leaf growth. Adenosine in a preferred embodiment does not require these cautions. Additionally, adenosine had no negative effects on mandarin fruit quality and in one of the three years of the research described in Example 2, had the desirable effects of reducing acidity and increasing the ratio total of soluble solids (sugars) to acid (See, Table 2-5).

The present disclosure is compatible with the standard practices of the citrus, avocado, pistachio and other evergreen and deciduous tree fruit and nut crops. Although plant growth regulators, biostimulants, nutritional supplements and fertilizers are all subject to varying degrees of regulation by the Federal Environmental Protection Agency and state agencies, the active ingredients of the disclosure are readily available natural metabolites. Moreover, since 6-benzyladenine (6-BA) has been previously exempted from the requirement of a residue tolerance for use on apple and pistachio, adenosine and precursors thereof should be similarly exempted for use on these and other crops. Moreover, AMP, for which adenosine is a precursor, is a GRAS (Generally Recognized as Safe) compound.

Further methods for increasing production by Clementine mandarin trees by canopy application are as follows: (1) adenosine (25 mg/L) administered at 10% anthesis; (2) adenosine (25 mg/L) administered at full bloom; (3) adenosine (25 mg/L) administered 30 days after 75% petal fall; (4) adenosine (25 mg/L) administered at full bloom and 30 days after 75% petal fall; (5) adenosine (50 mg/L) administered at 10% anthesis; (6) adenosine (50 mg/L) administered at full bloom; (7) adenosine (50 mg/L) administered 30 days after 75% petal fall; and (8) adenosine (50 mg/L) administered at full bloom and 30 days after 75% petal fall to increase fruit set. These methods are expected to compare favorably to untreated controls, as well as standard available practices: (9) $GA_3$ (PROGIBB® 4% from Valent BioSciences Corp.) at 1-8 fluid oz per 100 gallons of water, using a sufficient number of gallons for good coverage; 1-2 applications from 50% petal fall to 3 weeks after petal fall of mandarins and mandarin hybrids. Unless otherwise stated, all treatments are in two gallons of water per tree. There are 15 individual tree replicates per treatment in test methods. At harvest, fruit production is assessed (kg fruit per tree, fruit number per tree and fruit quality).

C. Methods of Increasing Avocado Production

Exemplary methods for increasing the production of avocados are provided in Example 3 and briefly summarized below. In some embodiments, the methods involve administering a composition comprising adenosine by trunk injection of 'Hass' avocado trees. The following treatments were injected (1 g per tree) in mid-January into the trunk of on-crop 'Hass' avocado trees in a commercial orchard in Irvine, Calif.: (1) adenosine (Sigma Chemical); (2) 6-BA (Sigma Chemical); (3) $GA_3$ (PROGIBB 40%, Valent Bio-Sciences Corp.); (4) TIBA (Sigma Chemical); and (5) TIBA plus adenosine. Each material was supplied at the rate of 1 g per tree dissolved in 50-60 ml distilled water using two plastic syringes per tree. In test methods there were five individual tree replicates per treatment, including (6) untreated on-crop control trees. For each tree, branches (12 inches long), 1 with fruit and 1 branch without fruit in each of the four tree quadrants, were tagged. During spring bloom, the number of floral shoots (indeterminate and determinate), vegetative shoots and inactive buds on each tagged branch were counted. The methods of the present disclosure for increasing avocado production through administration of a composition comprising adenosine are expected to compare favorably to untreated controls, as well as foliar or soil applied fertilization strategies. At present only one plant growth regulator, naphthalene acetic acid (NAA) to inhibit shoot growth after pruning, is registered for use on avocado in the United States. From the results presented in Table 3-1, the use of adenosine to increase crop production is contemplated to compare favorably to the use of plant growth regulators in other deciduous fruit crops. In particular an increase in avocado production is achievable by increasing bud break, which increases flower number and fruit number and by increasing flower and fruit retention. Other suitable methods for administration of compositions comprising adenosine to avocado trees include use of a foliar spray to 25 to 50 mg/L in 250 to 500 gallons of water per acre applied at (1) full bloom/anthesis; or (2) when fruit are 17-20 mm in diameter, just prior to the exponential increase in fruit size [late June to early July].

II. Compositions for Increasing Crop Production

The present disclosure provides compositions comprising a natural metabolite for increasing crop production, which includes increasing aspects of one or both of vegetative and reproductive growth. In some embodiments, the natural metabolite comprises one or more of adenosine, adenosine phosphates (AMP, ADP, ATP) inosine, inosine phosphates (IMP, IDP, ITP) adenine, hypoxanthine, and xanthine. In the following description unless otherwise indicated the specified months for application of the compositions of the present disclosure refer to a southern California climate and season. One of skill in the art will be able to easily modify the disclosed technology for other growth conditions (e.g., southern hemisphere).

Adenosine (and adenine) is an ubiquitous metabolite that serves as a precursor in all living organisms for the synthesis of DNA, RNA and ATP (energy currency of all living organisms). In plants, adenosine also serves as a precursor to the synthesis of cytokinins. As such, adenosine and the like may be properly categorized as nutritional supplements, and therefore could be formulated for use by organic growers, who have access to few growth enhancers. Additionally, adenosine can also increase fruit retention, shoot development and spring bud break to increase floral intensity and total yield. As such in some embodiments, the compositions comprising adenosine can be formulated for use as a plant growth regulator. The compositions of the present disclosure are suitable for use to increase crop production of a variety of perennial and annual fruit crops including but not limited to citrus, avocado, pistachio, pecan, apricot, peach, plum, tomato, pepper, strawberry, raspberry and blueberry.

At present there are only two plant growth regulators registered for use on mandarins in California, gibberellic acid ($GA_3$) for increasing fruit set (retention of young fruit) and 2,4-dichlorooxyacetic acid (2,4-D) for increasing fruit size (UC Pest Management Guidelines, www.ipm.ucdavis.edu/PMG/r107900111.html). Recent research (Chao and Lovatt, Final Report to the Citrus Research Board, 2007) indicates that, in a light crop year (approximately 550 fruit per tree), it was beneficial to apply $GA_3$ early (starting at 60% bloom), frequently (four applications) and at a higher rate (15 or 25 mg $GA_3$/L) to successfully increase the total number of fruit per tree, but not total yield as kilograms fruit per tree, and to increase the yield of commercially valuable large size fruit (packing carton sizes large, jumbo and mammoth) as both kilograms and number per tree. In the on-crop year (approximately 1200 fruit per tree), it was better not to apply $GA_3$. In the on-crop years studied, $GA_3$ treatments either reduced both total yield and yield of commercially valuable large size fruit (packing carton sizes large, jumbo and mammoth) or had no effect. Use of 2,4-D to increase fruit size of mandarins carries the caution that it can cause fruit dryness in mandarin and mandarin hybrids, (e.g., especially 'Nules' Clementine), which tends to have a low juice content, or in orchards prone to granulation (UC Pest Management Guidelines, www.ipm.ucdavis.edu/PMG/r107900311.html). Therefore, there is room for new technology that increases mandarin fruit size. Moreover, the continued registration of 2,4-D as a PGR is under review (Federal Register, Vol. 73, No. 248, 2008). If the registration of 2,4-D is cancelled, a new PGR to increase size of navel and Valencia orange and mandarin fruit and prevent preharvest fruit drop will be essential.

Foliar fertilization can meet the plant's demand for a nutrient at times when soil conditions (low temperature, low soil moisture, pH, salinity) render soil-applied fertilizers ineffective. Thus, foliar fertilization is an effective method for correcting soil deficiencies and overcoming the soil's inability to transfer nutrients to the plant. Nutrients, especially phosphate, potassium and trace elements can become fixed in the soil and unavailable to plants. Applying nutrients directly to leaves, the major organ for photosynthesis, ensures that the plant's metabolic machinery is not compromised by low availability of an essential nutrient. The key to achieving a yield benefit and net increase in grower income is properly timing the foliar application of fertilizer to key stages of crop phenology when nutrient demand is likely to be high or when soil conditions are known to restrict nutrient uptake. For citrus and avocado tree crops, this approach is in contrast to applying foliar fertilizers at the standard time of ⅓- to ⅔-leaf expansion (March), which targets foliage with a thin cuticle and large surface area and only results in yields equal to those attained with soil-applied fertilizer (Embleton and Jones, J Environ Quality, 3:388-392, 1974; and Labanauskas et al., Proc 1st Intl Citrus Symp, 3:1535-1542, 1969).

For citrus preferred foliar fertilization treatments for use in combination with foliar applied adenosine (or the like) include but are not limited to the following treatments. (1) Nitrogen[23 lb/acre, urea (46% N, 0.25% biuret)] applied alone or with potassium and phosphorus [0.64 gal/acre, potassium phosphite (0-28-26)] in late winter (January or February) when adenosine is used to increase spring bud break to support flower development, fruit set and total yield, without reducing fruit size, and to increase total soluble solids (TSS) and TSS to acid ratio. (2) Zinc [1 lb/acre, $ZnSO_4$ (36% Zn)] at 10% anthesis in the southwest tree quadrant (SWTQ) when adenosine is used to increase fruit set and total yield, without reducing fruit size, since due to colder soils Zn can be limiting at this time. (3) Boron[1.3 lb/acre, Solubor (20.5% B)] at 10% anthesis in the SWTQ when adenosine is used to increase fruit set, total yield and yield of commercially valuable large size fruit, since boron can be limiting in the ovary and can compromise fruit set even in plants that show adequate boron by standard tissue analyses. (4) Potassium and phosphorus [0.49 gal/acre, potassium phosphite (0-28-26)] in May and July when adenosine is applied at 75% petal fall in the NWTQ, 10 days after 75% petal fall in the NWTQ, or applied at maximum peel thickness to obtain a synergistic effect in increasing yield of commercially valuable large size fruit, without reducing total yield, and to increase TSS and TSS to acid ratio and to support summer vegetative shoot growth to increase inflorescence number the next spring and total yield the following year. (5) Nitrogen[23 lb/acre, urea (46% N, 0.25% biuret)] at maximum peel thickness when adenosine is applied at 75% petal fall in the NWTQ, 10 days after 75% petal fall in the NWTQ, or applied at maximum peel thickness to obtain a synergistic effect in increasing yield of commercially valuable large size fruit, without reducing total yield, and to increase TSS and TSS to acid ratio and to support summer vegetative shoot growth to increase inflorescence number the next spring and total yield the following year. (6) Potassium nitrate (25 lb $KNO_3$/acre) at dormancy (February), post-bloom (~April) and exponential fruit growth (July-August) when adenosine is applied at one or more of the preferred application times to provide nitrogen and potassium to support growth of commercially valuable large size fruit.

For pistachio, adenosine is applied with a foliar fertilizer at bud swell to green tip for emerging inflorescences (late February to early March) to enhance flower nutrient levels (ovary and/or pollen) to increase fruit (nut) set. Exemplary treatments include: (1) Nitrogen[6 lbs/acre, urea (46% N, 0.25% biuret)]; (2) Nitrogen[6 lbs/acre, urea (46% N, 0.25% biuret)] combined with zinc [5 lb/acre, $ZnSO_4$ (36% Zn)]; (3) Boron[5 lb/acre, Solubor (20.5% B)]; or (4) Nitrogen [6 lbs/acre, urea (46% N, 0.25% biuret)] combined with zinc [5 lb/acre, $ZnSO_4$ (36% Zn)] and boron[5 lb/acre]. Adenosine (or the like) is applied with foliar fertilizer at ½ to ⅔ leaf expansion when leaves have a cuticle thin enough for nutrient uptake and sufficient surface area that the amount of nutrient taken up is large enough to impact tree physiology and fruit (nut) set and nut size: (1) Zinc [2 lb/acre, $ZnSO_4$ (36% Zn)]; (2) Nitrogen[6 lbs/acre, urea (46% N, 0.25% biuret)]; or (3) Zinc [2 lb/acre, ZnSO$_4$ (36% Zn)] and nitrogen[6 lbs/acre, urea (46% N, 0.25% biuret)] combined. Adenosine (or the like) is applied with foliar fertilizer in early June, early July and mid-August to enhance kernel filling: (1) Potassium[10 lb/acre, KTS (0-0-25-17S)]; (2) Potassium[10 lb/acre, KNO$_3$ (13-0-38)]; (3) Nitrogen[6 lbs/acre, urea (46% N, 0.25% biuret)]; or (4) Potassium[10 lb/acre, KTS (0-0-25-17S)] and nitrogen[6 lbs/acre, urea (46% N, 0.25% biuret)] combined.

For avocado, suitable treatments comprising adenosine and a foliar fertilizer are as follows. (1) Boron applied at 1.45 lb in 200 gallons of water per 110 trees per acre (1.63 kg B in 1869 L/ha) or urea-nitrogen at 50 lb (46-0-0, ≤0.25% biuret; 23 lb N) in 200 gallons water per acre (25.8 kg N in 1869 L/ha) just prior to avocado inflorescence expansion (cauliflower stage of inflorescence development) to increase the number of viable ovules and increased the number of pollen tubes that reach the ovules (Jaganath and Lovatt, Acta Hort, 1:181-184, 1998). (2) Potassium phosphite [Nutri-Phite, 0-28-26; 2.6 quarts in 200 gallons water per acre (6 L Nutri-Phite in 1869 L/ha)] at the cauliflower stage of inflorescence development (Gonzalez et al., in press). Not all nutrients are taken up through the foliage of all crop species and, even if taken up, some nutrients are not phloem mobile. Whereas the developing inflorescence of the 'Hass' avocado takes up canopy-applied fertilizers, leaves of the 'Hass' avocado, especially under California growing conditions, do not take up many nutrients efficiently. However, production benefits are obtained by properly timing soil nitrogen applications at 25 lb nitrogen as ammonium nitrate per acre (56 kg/ha) to three critical stages of tree phenology: (1) anthesis-early fruit set and initiation of the vegetative shoot flush at the apex of indeterminate floral shoots (about mid-April); (2) period of rapid cell division and significant increase in fruit size (late June to early July); and (3) inflorescence initiation (late July to early August). Adenosine (or the like) is administered as a soil/irrigation application, foliar application or trunk injection during one or more of the following time periods: (1) in late winter (January or February) to increase spring bud break, floral intensity, fruit set and total yield; (2) at the cauliflower stage of inflorescence development or full bloom to increase fruit set and total yield; (3) at late June to early July to reduce June drop and increase fruit growth to increase fruit size and yield of commercially valuable large size fruit, reduce pre-harvest fruit drop and stimulate summer vegetative shoot growth to increase the number of inflorescences the next spring; and (4) early August to prevent pre-harvest, support summer shoot growth, and increase fruit growth of the current crop to increase fruit size and yield of commercially valuable large size fruit.

The natural metabolite (adenosine and the like) of the present disclosure may be formulated with one or more of a pH stabilizer, an anti-oxidant (or other compound for increasing shelf life), and a bioactive agent (e.g., insecticide, fungicide, bactericide, and/or acaricide). In addition, the natural metabolite can be formulated in a mixture with a carrier or, if necessary, other auxiliary agents to form any one of the standard types of preparations commonly used in agriculture, for example, a dry blend, granules, a wettable powder, an emulsion, an aqueous solution and the like.

Suitable solid carriers are clay, talc, kaolin, bentonite, terra abla, calcium carbonate, diatomaceous earth, silica, synthetic calcium silicate, kieselguhr, dolomite, powdered magnesia, Fuller's earth, gypsum and the like. Solid compositions can also be in the form of dispersible powders or grains, comprising, in addition to the natural metabolite, a surfactant to facilitate the dispersion of the powder or grains in liquid.

Liquid compositions include solutions, dispersions or emulsions containing the natural metabolite (adenosine and the like) together with one or more surface-active agents (surfactants) such as wetting agents, dispersing agents, emulsifying agents, or suspending agents. In those applications in which the compounds are applied as a foliar spray, surfactants are preferably used. Surfactants reduce the surface tension in the spray droplet to ensure that the material applied spreads out and covers the leaf surface rather than beading up. This facilitates absorption of the applied material into the plant. Surfactants can also affect the uptake of materials directly by changing the viscosity and crystalline structure of the waxes on the surface of the leaf or other tissues (Tu and Randall, Chapter 8-Adjuvants. In: Tu et al., [Eds.] Weed Control Methods Handbook: Tools and Techniques For Use In Natural Areas. The Nature Conservancy p. 219, 2001).

Generally, any number of surfactants may be used consistent with the purpose of this constituent. For example the surfactant can comprise a nonionic, anionic, cationic, or zwitterionic surfactant. The surfactant can be present in the composition of the disclosure as formulated or, alternatively, the surfactants can be introduced during administration to the plant. In such an instance, regardless of whether the administration is conducted via automated or manual means, the surfactant can be combined with the composition of the disclosure prior to, or co-dispensed separately. Cationic surfactants useful in compositions of the disclosure include but are not limited to amine ethoxylates, amine oxides, mono- and dialkylamines, imidazolinium derivatives, and alkylbenzyldimethylammonium halides. Nonionic surfactants useful in the context of this disclosure are generally polyether (also known as polyalkylene oxide, polyoxyalkylene or polyalkylene glycol) compounds. More particularly, the polyether compounds are generally polyoxypropylene or polyoxyethylene glycol compounds. Anionic surfactants useful with the disclosure comprise, for example, alkyl carboxylates, linear alkylbenzene sulfonates, paraffin sulfonates and secondary n-alkane sulfonates, sulfosuccinate esters and sulfated linear alcohols. Zwitterionic or amphoteric surfactants useful with the disclosure include but are not limited to alpha-N-alkylaminopropionic acids, n-alkyl-alpha-iminodipropionic acids, imidazoline carboxylates, amine oxides, sulfobetaines and sultaines.

Although the surfactant can be present in the composition in any useful amount, in preferred embodiments, it is present in an amount from about 0.01% to about 25%, more preferably from about 0.01% to about 10% and more preferably still from about 0.05% to about 5%. A surfactant is present in the compositions of the disclosure in a useful amount when it facilitates the dissolution of the natural metabolite, enhances its uptake by the plant, and/or its effectiveness in inducing the desired response. In a preferred embodiment, the surfactant is a polysorbate, which is present in an amount from about 0.05% to about 5%. In a particularly preferred embodiment, the surfactant is polysorbate 20 (polyoxyethylene 20 sorbitan monolaurate), which is present in the composition in an amount from about 0.05% to about 5%.

The compositions of the disclosure can also contain suspending agents. Suitable suspending agents are, for example, hydrophilic colloids, for example polyvinylpyrrolidone and sodium carboxymethylcellulose, and the vegetable gums, for example, gum acacia and gum tragacanth.

Aqueous solutions, dispersions or emulsions may be prepared by dissolving the natural metabolite (adenosine or the like) in water or an organic solvent which can, if desired, contain one or more surface active, sticking, wetting, dispersing, or emulsifying agents. Suitable organic solvents are, for example, alcohols, hydrocarbons, oils and sulfoxides. In embodiments using alcohols, methanol, isopropyl alcohol, propylene glycol and diacetone alcohol are preferred. In embodiments using oils, petroleum oils are preferred. Of the sulfoxides, dimethylsulfoxide is preferred.

The compositions which are to be used in the form of aqueous solutions, dispersions or emulsions are generally supplied in the form of a concentrate containing a high proportion of the natural metabolite (adenosine or the like), and the concentrate is then diluted with water before use. These concentrates are usually required to withstand storage for prolonged periods and after such storage, to be capable of dilution with water in order to form aqueous preparations that remain homogeneous for a sufficient time to enable them to be applied by conventional spray equipment. In general, concentrates can conveniently contain from 10 to 60 percent by weight of the natural metabolite (adenosine or the like).

Exemplary bioactive compounds with which compositions of the present disclosure can be formulated include but are not limited to: insecticides such as abamectin, acephate, acetamiprid, avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, oxamyl, parathion, parathion-methyl, permethrin, phorate, phosalone, phosmet, phosphamidon, pirimicarb, profenofos, pymetrozine, pyridalyl. pyriproxyfen, rotenone, spinosad, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), myclobutanil, neoasozin (ferric methanearsonate), oxadixyl, penconazole, pencycuron, probenazole, prochloraz, propamocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; and acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad. A general reference for these agricultural protectants is The Pesticide Manual, 12th Edition, Tomlin, Ed., British Crop Protection Council, Farnham, Surrey, United Kingdom, 2000.

EXPERIMENTAL

The following examples are provided in order to demonstrate and further illustrate certain preferred embodiments and aspects of the present disclosure, and are not to be construed as limited the scope thereof.

Abbreviations. To ensure a complete understanding of this disclosure, the following abbreviations are provided: ABA (abscisic acid); Ado (adenosine); 6-BA (benzylaminopurine or benzyladenine); 2,4-D (2,4-dichlorophenoxyacetic acid); 2,4,5-T (2,4,5-trichlorophenoxyacetic acid); GA (gibberellin); $GA_3$ (gibberrillic acid); IAA (indole-3-acetic acid); IBA (indole-3-butyric acid); IPA (isopentenyladenine); NAA (1-naphthaleneacetic acid); TIBA (2,3,5-triiodobenzoic acid); PGR (plant growth regulator); and Veg (vegetative).

Statistical Analysis. All data were reported as mean number of shoots per 100 nodes unless stated otherwise. Analysis of variance was used to test treatment effects on vegetative and floral shoot growth, floral intensity as the production of leafless and leafy floral shoots of mandarin and determinate and indeterminate floral shoots of avocado and vegetative shoots of both crop plants at bloom and yield of mandarin using the General Linear Models procedure of the SAS statistical program (SAS Inst. Inc., Cary, N.C.). Means were separated using Fisher's protected LSD, Duncan's multiple range test or Dunnett's two-tailed T-test at $P=0.05$.

Example 1

Administration of Adenosine by Irrigation to Increase Tomato Production

This example describes the increase in fruit production by tomato plants (cv. Supersweet 100), achieved via application of adenosine by irrigation. Adenosine (9-beta-D-adenosine) obtained from Sigma Chemical Co. (Catalog No. A9251) was applied in a sufficient amount of distilled water to move the material into the root zone of 'Supersweet 100' tomato plants. Plants receiving treatments 2 and 3 were treated once every 10 days. Plants receiving treatments 4, 5, 6, and 7 were treated daily. The total amount of cytokinin or adenosine received by plants in each treatment by the end of experiment (75 days after planting) is given in parenthesis in the Table 1-1 below. The IPA concentration of the vermicompost tea was determined by radioimmunoassay.

TABLE 1-1

Effect of adenosine, the cytokinins isopentenyladenine (IPA) and 6-benzyladenine (6-BA), and vermicompost tea on vegetative and reproductive growth of tomato plants

| Treatment[y] | # Leaves | Main Shoot (mm) | Tap Root (mm) | # Veg. shoots | # Fruiting shoots | # Fruit | Fruit diameter mm |
|---|---|---|---|---|---|---|---|
| | | | average value per plant | | | | |
| (1) Control | 39 e [x] | 78.50 | 26.50 | 12.20 e | 3.80 e | 8 c | 14.98 d |
| (2) Vermicompost tea (0.049 µg IPA) | 67 d | 46.50 | 44.50 | 23.40 d | 10.20 d | 9 c | 19.36 c |
| (3) Vermicompost tea (0.49 µg IPA) | 107 ab | 70.00 | 24.75 | 34.20 b | 17.60 a | 17 a | 21.87 b |
| (4) IPA (0.035 µg) | 99 abc | 73.75 | 25.50 | 30.20 c | 12.40 bc | 13 ab | 21.81 b |
| (5) IPA (0.35 µg) | 87 c | 81.00 | 20.25 | 30.80 c | 11.60 cd | 10 bc | 19.92 c |
| (6) 6-BA (0.35 µg) | 92 bc | 74.50 | 21.00 | 31.00 bc | 14.40 b | 9 c | 21.51 b |
| (7) Adenosine (0.35 µg) | 111 a | 74.00 | 28.00 | 38.00 a | 17.60 a | 15 a | 24.13 a |
| P-value | <.0001 | 0.1282 | 0.1081 | <.0001 | <.0001 | 0.0008 | <.0001 |

[z] The experiment was a randomized complete block design with four replications per treatment and seven treatments, plants were harvested at the end of 75 days.
[y] Treatments were applied in a sufficient amount of distilled water to move the material into the root zone. Plants receiving treatments 2 and 3 were treated once every 10 days. Plants receiving treatments 4, 5, 6, and 7 were treated daily. The total amount of cytokinin or adenosine received by plants in each treatment by the end of experiment (75 days) is given in parentheses. The IPA concentration of the vermicompost tea was determined by radioimmunoassay.
[x] Means within a vertical column followed by different letters are significantly different by Fisher's Protected LSD at P = 0.05.

The data indicate that adenosine significantly increased the number of lateral vegetative shoots and lateral reproductive shoots, number of leaves, number of fruit and diameter of fruit of tomato plants compared to equal concentrations of 6-benzyladenine and isopentenyladenine. Adenosine, however, did not have a general effect on plant growth as it did not significantly alter the length of the main shoot or the tap root. That the effective concentration of adenosine was higher than the effective concentration of IPA is consistent with adenosine functioning as a nutritional supplement and not a PGR like IPA. The results demonstrate the capacity of adenosine to increase crop production. In this example, adenosine stimulated bud break to increase lateral branching and to increase the number of lateral vegetative shoots. The effect of adenosine in increasing bud break and increasing lateral branching also had a very positive effect on increasing the number of reproductive shoots, the number of flowers and the number of fruit set (retained). Adenosine resulted in a net increase in the number of fruit per plant of 87.5% over the untreated control. In addition to increasing fruit number, adenosine significantly increased the size of individual fruit (e.g., increased transverse diameter). Adenosine increased the average size of individual tomato fruit by 61% over that of fruit from untreated control plants. The effect of adenosine on shoot growth resulted in a significant increase in the number of leaves per plant. Adenosine treated plants had 2.85-fold more leaves than untreated control plants.

Example 2

Administration of Adenosine by Foliar Spray to Increase Mandarin Production

This example describes the increase in the number and yield of commercially valuable fruit of Clementine mandarin trees achieved by canopy application of adenosine. Adenosine (9-beta-D-adenosine) obtained from Sigma Chemical Co. (Catalog No. A9251) was applied (25 mg/L in 250 gallons of water per acre; 23.66 g/acre) with a 400 psi handgun sprayer one time at maximum peel thickness, which marks the end of the cell division stage of citrus fruit development, to 'Fina Sodea' Clementine mandarin trees. As shown in Table 2-1 below, application of adenosine significantly increased the 3-year cumulative number of fruit 57.16 to 69.85 mm in diameter (packing carton sizes large and jumbo) and increased the 3-year cumulative number of commercially valuable mandarin fruit in the combined pool for fruit of packing carton sizes large, jumbo and mammoth without reducing total yield (average number of fruit per tree) (P≤0.05). As shown in Table 2-2 below, application of adenosine significantly increased the 3-year cumulative yield of fruit 57.16 to 69.85 mm in diameter (packing carton sizes large and jumbo) and increased the 3-year cumulative yield of commercially valuable mandarin fruit in the combined pool for fruit of packing carton sizes large, jumbo and mammoth without reducing total yield (average kilograms [quantity×size] per tree) (P≤0.05). These data were also significant (P≤0.05) when averaged across the 3 years of the experiment, establishing that adenosine had a positive effect each year. Adenosine did not have a negative effect on fruit quality in any year of the study. In year three of the study, fruit from adenosine-treated trees had significantly reduced juice acid (P=0.0163), which resulted in a higher total soluble solids to acid ratio of the juice (P=0.0570) (Tables 2-4a-c).

TABLE 2-1

Effect of adenosine applied to the canopy of mandarin trees on fruit quantity

| Treatment | Total | Colossal | Mammoth | Jumbo | Large | Medium | Small | Ma + J + L |
|---|---|---|---|---|---|---|---|---|
| | | | | Total fruit no./tree | | | | |
| Adenosine | 1529.3[y] | 5.64 | 22.89 | 128.25 a | 360.93 a | 497.05 | 417.12 | 512.07 a |
| Control | 1467.0 | 6.78 | 26.94 | 86.53 b | 292.66 b | 493.79 | 431.69 | 406.14 b |
| T-test | NS | NS | NS | * | * | NS | NS | * |

[z]Fruit size categories based on fruit transverse diameters (mm): small (44.45-50.80), medium (50.81-57.15), large (57.16-63.50), jumbo (63.51-69.85), mammoth (69.86-76.20), colossal (76.21-82.55), and large + jumbo + mammoth (57.16-76.20). Ma + J + L is the sum of mammoth, jumbo and large fruit.
[y]Average fruit numbers followed by different letters are significantly different at P = 0.05. indicated by an asterisk or not significantly indicated by NS based on Dunnett's two-tailed T-test.

TABLE 2-2

Effect of adenosine applied to the canopy of mandarin trees on fruit yield (quantity x mass)

| Treatment | Total | Colossal | Mammoth | Jumbo | Large | Medium | Small | Ma + J + L |
|---|---|---|---|---|---|---|---|---|
| | | | | Total kg/tree | | | | |
| Adenosine | 126.30[y] | 1.04 | 3.52 | 15.42 a | 34.67 a | 37.00 | 23.58 | 53.60 |
| Control | 110.88 | 1.28 | 4.15 | 10.47 b | 28.24 b | 36.94 | 24.37 | 42.86 |
| T-test | NS | NS | NS | * | * | NS | NS | * |

[z]Fruit size categories based on fruit transverse diameters (mm): small (44.45-50.80), medium (50.81-57.15), large (57.16-63.50), jumbo (63.51-69.85), mammoth (69.86-76.20), colossal (76.21-82.55), and large + jumbo + mammoth (57.16-76.20). Ma + J + L is the sum of mammoth, jumbo and large fruit.
[y]Average weights followed by different letters are significantly different at P = 0.05 indicated by an asterisk or not significantly different indicated by NS based on Dunnett's two-tailed T-test.

TABLE 2-3

Effect of adenosine applied to the canopy of mandarin trees on fruit value (cumulative income in U.S. dollars).

| Treatment | Total[y] | Small | Medium | Large | Jumbo | Mammoth | Ma + J + L |
|---|---|---|---|---|---|---|---|
| | | | US$/acre based on 200 trees/acre | | | | |
| Adenosine | 8015.80 | 1497.80 | 2522.40 | 2584.10 a | 1149.50 a | 262.10 | 3995.60 a |
| Control | 7264.50 | 1550.90 | 2518.60 | 2105.20 b | 780.70 b | 309.10 | 3195.00 b |
| P-value | 0.1179 | 0.8130 | 0.9088 | 0.0723 | 0.0737 | 0.6982 | 0.0645 |
| Dunnett | NS | NS | NS | * | * | NS | |

[z]Fruit size categories based on fruit transverse diameters (mm): small (44.45-50.80), medium (50.81-57.15), large (57.16-63.50), jumbo (63.51-69.85), mammoth (69.86-76.20), and large + jumbo + mammoth (57.16-76.20). Fruit were packed by number (based on size) per 11 kg box. Fruit count per box was: small, 44; medium; 34, large, 26; jumbo, 20; and mammoth 15. Average US dollars per box (retail) of fruit of each size category was: small, $3.50; medium, 3.75; large, $4.10; jumbo, $4.10; mammoth, $4.10; Ma + J + L is the sum of mammoth, jumbo, and large fruit.
[y]Total is the sum of small, medium, large, jumbo, and mammoth values.
* Values differ significantly from that of the control based on two-tailed Dunnett's test at P = 0.05.

These data highlight the benefits of adenosine applied at maximum peel thickness. There was a statistically significant net increase in 3-year cumulative yield of commercially valuable large fruit (57.16-76.20 mm in diameter) of 4,735 lbs/200 trees/acre. These data were also significant when averaged across the three years of the experiment using repeated measures analysis, establishing that adenosine had a positive effect each year. There was no reduction in total yield; the adenosine-treated trees had a numerical (non-significant) net increase of 12,460 fruit/200 trees/acre/3 years, equaling 6,799 lbs fruit/200 trees/acre/3 yrs.

Use of foliar-applied adenosine to increase fruit number and to increase the yield (quantity×size) of commercially valuable fruit is expected to compare favorably to untreated controls, as well as standard available practices: (1) GA$_3$ (PROGIBB® 4%, Valent BioSciences Corp.) at 1-8 fluid oz per 100 gallons of water, using a sufficient number of gallons for good coverage; 1-2 applications from 50% petal fall to 3 weeks after petal fall of mandarins and mandarin hybrids; (2) 2,4-D (CITRUSFIIX® AmVac Corp.) 0.67 oz (3.34 lbs 2,4-D isopropylester/gallon) per 100 gallons of water at 500 gallons per acre 21 to 35 days after 75% petal fall of mandarins and mandarin hybrids; and (3) 1% low-biuret urea applied at maximum peel thickness. ProGibb® must be used with caution as it may result in more fruit set than is desirable thereby reducing final fruit size, and leaf drop may occur in trees under stress. Adenosine does not require this caution and its efficacy in increasing yield of commercially valuable fruit is not as sensitive to crop load (alternate bearing) as that of GA$_3$. Similarly, CITRUSFIX® must be used with caution as it can cause fruit dryness (especially in 'Nules' and other cultivars that tend to be dry or granulated). In addition, CITRUSFIX® cannot be used on trees less than 6 years old and cannot be used during a flush of leaf growth.

Again adenosine does not require these cautions. Adenosine did not have negative effects on mandarin fruit quality. Moreover, in one of the three years of the research adenosine had the desirable effects of reducing acidity and increasing the ratio total soluble solids (sugars) to acid.

Example 3

Administration of Adenosine by Trunk Injection to Increase Avocado Production

This example describes the use of adenosine to increase spring bud break of 'Hass' avocado trees to increase floral intensity and avocado production. Increased bud break was achieved via trunk injection of adenosine (9-beta-D-adenosine) obtained from Sigma Chemical Co. (Catalog No. A9251), alone or with a plant growth regulator. The following treatments were injected (1 g/tree) in mid-January into the trunk of on-crop 'Hass' avocado trees in a commercial orchard in Irvine, Calif.: (1) adenosine (Sigma); (2) 6-BA (Sigma); (3) $GA_3$ (ProGibb 40%, Valent BioSciences Corp.); (4) TIBA (Sigma); and (5) TIBA plus adenosine. Each material was supplied at the rate of 1 g per tree dissolved in 50 to 60 ml distilled water using two plastic syringes per tree. There were five individual tree replicates per treatment, including (6) untreated on-crop control trees. For each tree, branches (12 inches long), 1 with fruit and 1 branch without fruit in each of the four tree quadrants, were tagged. During spring bloom, the number of floral shoots (indeterminate and determinate), vegetative shoots and inactive buds on each tagged branch were counted.

TABLE 3-1

Effect of trunk injections on spring bloom of 'Hass' avocado trees bearing an on-crop

| Treatment | Time | Floral | Determinate Floral | Indeterminate Floral | Floral (with fruit) | Floral (w/o fruit) |
|---|---|---|---|---|---|---|
| | | | | No. of shoots per 100 nodes | | |
| On-crop control | January | 6 b$^z$ | 1 b | 5 | 5 c | 7 |
| Ado | January | 10 ab | 3 ab | 7 | 8 abc | 10 |
| 6-BA | January | 9 b | 1 b | 8 | 9 abc | 9 |
| $GA_3$ | January | 7 b | 2 b | 6 | 6 bc | 8 |
| TIBA | January | 9 b | 1 b | 8 | 11 ab | 8 |
| Ado + TIBA | January | 15 a | 8 a | 7 | 12 a | 16 |
| P-value | | 0.0693 | 0.0789 | 0.2906 | 0.0793 | 0.1618 |

$^z$Means within a column followed by a different letter are significantly different at specified P-value by Fisher's Protected LSD Test.

Table 3-1 summarizes the effect of January adenosine and plant growth regulator (PGR) trunk injections on spring bloom of 'Hass' avocado trees bearing an on-crop. These results indicate that adenosine applied with TIBA as a single trunk injection to on-crop trees in January overcame the inhibitory effect of the fruit on bud break in spring and significantly increased the number of floral shoots compared to the untreated on-crop control trees. The treatment significantly increased the number of determinate floral shoots (inflorescences), which are typically in low number or absent in the off-crop year bloom. Moreover, the treatment significantly increased floral shoot number on the branches bearing fruit, bringing the number of floral shoots on branches with fruit, where the fruit have a direct inhibitory effect on buds, to that of branches without fruit, where inhibition of bud break would be expected to be less. Note that the efficacy of adenosine alone was equal to that of adenosine plus TIBA in increasing the total number of floral shoots per 100 nodes, but was not significantly different from the untreated on-crop control. Adenosine administered at a higher rate in January or administered at the same rate in July and again in January is contemplated to increase total floral shoot number to a value significantly greater than the untreated on-crop control trees at $P \leq 0.05$.

Various modifications and variations of the present disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are understood by those skilled in the art are intended to be within the scope of the claims.

I claim:

1. A method of increasing crop production, comprising administering to a crop plant a composition comprising a fertilizer and an effective amount of a nucleoside comprising adenosine, wherein said composition does not contain other nucleosides, and wherein said nucleoside comprises at least 75% 9 beta-D-adenosine (9BDA).

2. The method of claim 1, wherein the composition further comprises one or both of a plant growth regulator, and a biostimulant.

3. The method of claim 1, wherein the fertilizer is selected from the group consisting of nitrogen, potassium, magnesium, phosphorus, calcium, sulfur, iron, boron, chlorine, manganese, zinc, copper, molybdenum, nickel, cobalt, silicon, selenium, and combinations thereof.

4. The method of claim 1, wherein the crop plant is a perennial fruit plant.

5. The method of claim 4, wherein the perennial fruit plant is selected from the group consisting of apple, apricot, avocado, citrus, peach, pear, pecan, pistachio, and plum.

6. The method of claim 4, wherein the composition is administered at one or more of the following times: (i) at 10% anthesis, (ii) at full bloom, (iii) 30 days after 75% petal fall, (iv) at maximum peel thickness of the fruit, and (v) greater than 60 days before fruit harvest.

7. The method of claim 1, wherein the crop plant is an annual crop plant.

8. The method of claim 7, wherein the annual crop plant is selected from the group consisting of celery, spinach, and tomato.

9. The method of claim 7, wherein the composition is administered, one, two, three, four, five, six or seven times per week.

10. The method of claim 1, wherein the composition is administered by a technique selected from the group consisting of foliar spray, irrigation, and trunk injection.

11. The method of claim 1, wherein the increased crop production comprises an increase in reproductive growth.

12. The method of claim 11, wherein the increase in reproductive growth comprises an increase of one or more of the group consisting of number of fruiting shoots, number of fruit, fruit size, and total yield of fruit.

13. The method of claim 11, wherein the increase in reproductive growth comprises an increase in yield of commercially valuable large fruit on a per plant or per plot basis.

14. The method of claim 1, wherein the increased crop production comprises an increase in vegetative growth, wherein the increase in vegetative growth comprises an increase in one or both of number of leaves and number of vegetative shoots.

15. The method of claim 1, wherein the crop plant is a fruit tree.

16. The method of claim 1, wherein the crop plant is an orange tree.

17. The method of claim 1, wherein the crop plant is an avocado tree.

* * * * *